(12) United States Patent
Goloschapov et al.

(10) Patent No.: US 6,465,476 B1
(45) Date of Patent: Oct. 15, 2002

(54) IMMUNO-MODULATOR EXHIBITING ANTIMICROBIAL AND ANTI-MYCROBACTERIAL ACTIVITIES, METHOD FOR PRODUCING THE SAME AND PHARMACEUTICAL PREPARATION

(75) Inventors: Nikolai Mikhailovich Goloschapov; Elena Nikolaevna Goloschapova; Tamara Petrovna Filipskikh; Elena Andreevna Michurina; Ljubov Elizarovna Kostjuk, all of Moskovskaya obl., g. Sergiev-Posad; Rakhim Musaevich Khaitov, Moscow; Galina Ivanovna Tsyvkina, Vladivostok; Vladimir Kuzmich Grishin; Nikolai Alexandrovich Stukalov, both of Moskovskaya obl., g. Sergiev-Posad, all of (RU)

(73) Assignee: Alexandr Leonidovich Reshetov (RU)

( * ) Notice: Subject to any disclaimer, the term of this patent is extended or adjusted under 35 U.S.C. 154(b) by 0 days.

(21) Appl. No.: 09/485,779

(22) PCT Filed: Aug. 11, 1998

(86) PCT No.: PCT/RU98/00264

§ 371 (c)(1),
(2), (4) Date: Feb. 14, 2000

(87) PCT Pub. No.: WO99/07699

PCT Pub. Date: Feb. 18, 1999

(30) Foreign Application Priority Data

Aug. 11, 1997 (RU) .......................................... 97 114347

(51) Int. Cl.$^7$ ..................... C07D 239/60; A61K 31/513
(52) U.S. Cl. ......................................... 514/274; 544/310
(58) Field of Search .......................... 514/274; 544/319, 544/298, 310

(56) References Cited

FOREIGN PATENT DOCUMENTS

| CH | 396019 | 1/1966 |
| GB | 750194 | 6/1956 |
| SU | 322325 | 11/1972 |
| SU | 459228 | 9/1975 |

*Primary Examiner*—John M. Ford
(74) *Attorney, Agent, or Firm*—Kilpatrick Stockton LLP

(57) ABSTRACT

The present invention pertains to the field of medicine and more precisely relates to a novel immuno-modulator of the following formula

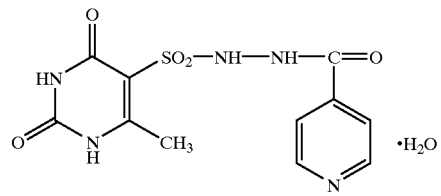

which exhibits anti-microbial and anti-mycobacterial activities. This modulator is produced by reacting equimolecular amount of 6-methyluracyl-5-sulphochloride and isoniazide in acetonitrile at a high temperature. The preparation is practically not toxic ($LD_{50}$ in severe conditions exceeding 7000 mg/kg) and can be used according to a given clinical tests for expressing the immuno-modulating and anti-mycobacterial activity. This preparation can be used for correcting various immuno-deficiencies including in HIV-infected patients as well as for treating mycobacterioses such as leprosy, tuberculosis, etc. This preparation can be administrated internally or parenterally. The compound described in the present invention represents the active substance of this pharmaceutical preparation, wherein said preparation can be used against secondary various immuno-deficiencies or mycobacterioses.

8 Claims, No Drawings

IMMUNO-MODULATOR EXHIBITING ANTIMICROBIAL AND ANTI-MYCROBACTERIAL ACTIVITIES, METHOD FOR PRODUCING THE SAME AND PHARMACEUTICAL PREPARATION

REFERENCE TO RELATED APPLICATION

This is a filing under 35 U.S.C. §371 based on PCT/RU98/002614 filed Aug. 11, 1998.

FIELD OF THE INVENTION

The present invention relates to the field of medicine and more precisely pertains to an immunomodulator exhibiting antimicrobial and antimycobacterial activities of the following formula:

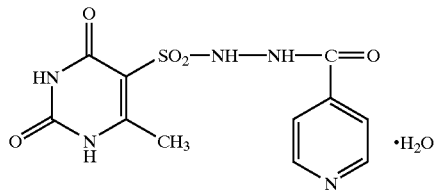

to a method for producing the same and to a pharmaceutical preparation for treating mycobacterioses as well as pulmonary chronic and nonspecific conditions, sexually transmitted diseases and the resulting immunodeficiency.

BACKGROUND OF THE INVENTION

The antileprous preparation diuciphonum (SU author's certificate No 459228) exhibits immunomodulating activities (SU author's certificate No 938442) and has an immunostimulating effect on humoral and cellular immunity (V. P.Leskov et al., "Clinical pharmacology for physicians", M., 1997, pp. 77–78; N. S. Prosorovsky, "Immunologic effects of diuciphonum and utilization of the latter for analyzing a proliferative response of lymphacytes", synopsis of a thesis for a candidate's degree in medicine, M., 1985; L. E. Kostyuk, "Immunocorrecting properties of antileprous preparations", synopsis of a thesis for a candidate's degree in biology, 1986). However, this preparation lacks mitogenetic activity of its own and is capable to increase the proliferation of T-cells only in response to phytohemagglutinin (PHA). The toxicity of diuciphonum amounts to 2600 mg/kg.

It is known that, although exerting an antibacterial action, N-(6-methyl-2,4-dioxo-1,2,3,4-tetrahydro-5-pyrimidinsulfon)-N'-isonicotinoylhydrazide (SU author's certificate No 768186) lacks immunotropic activity and, furthermore, it does not withstand prolonged storage conditions due to impurities contained therein. The immunomodulator exhibiting antimicrobial and antimycobacterial activities, the method for producing the same and the pharmaceutical preparation for treating secondary immunodeficiencies and resulting mycobacterioses which are claimed acording to the present invention are novel and have not been described in literature.

DISCLOSURE OF THE INVENTION

The problem taken as a starting point of the present invention is to provide a novel immunomodulator exhibiting antimicrobial and antimycobacterial activities, including the carriage of human immunodeficiancy virus (HIV), which immunomodulator is active not only in respect of mycobacteria of leprosy but also of those of tuberculosis as well as other deseases developing against the background of immunodeficiency, as well as to provide a method for producing this immunomodulator and a pharmaceutical preparation intended to be used at secondarty immunodeficiencies and mycobaterioses.

This problem is solved, in accordance with the present invention, by providing a novel immunomodulator exhibiting antimicrobial and antimycobacterial activities, this immunomodulator representing N-(6-methyl-2,4-dioxo-1,2,3,4-tetrahydro-5-pyridioxo-1,2,3,4-tetrahydro-5-pyrimidinsulfon)-N'-isonicotinoylhydrazide hydrate of the following formula:

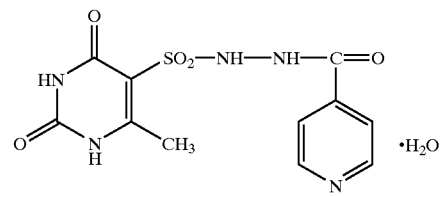

There is also provided a method for producing a novel immunomodulator exhibiting antimicrobial and antimycobacterial activities, which immunomodulator represents N-(6-methyl-2,4-dioxo-1,2,3,4-tetrahydro-5-pyrimidinsulfon)-N'-isonicotinoylhydrazide hydrate of the above formula.

According to the invention, the method of the present invention is carried out by reacting equimolecular amounts of 6-methyluracil-5-sulfochloride and isoniazide in acetonitrile at an elevated temperature. The pharmaceutical preparation for treating mycobacterioses, pulnonary chronic nonspecific conditions, sexually transmitted diseases and immunodeficiency, according to the present invention, comprises an immunomodulator exhibiting antimicrobial and antimycobacterial activities as the active substance, said immunomodulator representing N-(6-methyl-2,4-dioxo-1,2,3,4-tetrahydro-5-pyrimidinsulfon)-N'-isonicotinoylhydrazide hydrate of the above formula, and a vehicle.

The preparation isophonum claimed according to the present invention can be administered per os in any suitable medical form and parenterally. This preparation contains the active substance in amounts of 0.05 to 0.3 g.

As was shown by clinical tests, isophonum normalizes the immune status of persons suffering from leprosy, tuberculosis, chronic nonspecific pneumonia and chlamydiosis by involving the person's organism in the struggle against the disease; isophonum also stumulates the function of the cell by penetrating into it and carries the active substance as far as to the agent of disease and kills it. It is not ruled out that the preparation may have a direct effect on the sexually transmitted agents such as chlamydia, trichomonads, ureaplasmatic infection.

It should be stressed that isophonum is well tolerable, has no side effects and is compatible with modem antimycobacterial drugs (ethionamide, rifampicinum and others), this being supported by results of examination of leprous and tuberculous patients.

The toxicity of isophonum was determined on white unbred mice wheighing 18 to 20 g in an sharp experiment by Litchfild-Wilkokson's procedure and was found to exceed 7000 mg/kg.

DESCRIPTION OF THE BEST EMBODIMENT

The compound of the present invention is a white, sometimes a yellowish-hued light crystalline powder which is difficult to dissolve in water or usual organic solvents. It is soluble in dimethylformamide, dimethylsulfoxide, deluted acids and alkalies; f. p.=255–256° C. The structure of matter is confirmed by the data of PMR-spectroskopy.

The compound of the present invention and the pharmaceutical preparation on its basis were tested in an experiment carried out on animals and clinically on people.

Determination of immunotropic activity of isophonum was carried out. Immunotropic activity of isophonum was determined on a model of immunodeficiency caused by irradiation. To create an immunodeficient state the mice $F_1$ (CBA×C57BL/$_6$) were irradiated with gamma-rays on a radioterapeutic apparatus in a dose of 4 Gy (Gy is the irradiation unit gray) at an irradiation dose power of 0.55 Gr/min. The number of antibody-forming cells (AFC) in the spleens was calculated by Jeme-Nordin's procedure. Isophonum and diuciphonum were introduced per os over a wide range of doses. The investigation results are represented in Table 1.

TABLE 1

Influence of isophonum on the production of antibody-forming cells in irradiated animals

| Preparations, doses, μg per mouse | Number of mice in the group | AFC-number in the spleen | Immune response stimulation index | P |
|---|---|---|---|---|
| Irradiated controls | 18 | 308 ± 36 | — | — |
| Isophonum | | | | |
| 10 | 18 | 1013 ± 126 | 3.63 ± 0.57 | <0.001 |
| 100 | 18 | 1173 ± 125 | 4.28 ± 0.8 | <0.001 |
| 1000 | 18 | 1216 ± 124 | 4.46 ± 0.9 | <0.001 |
| Diuciphonum | | | | |
| 10 | 18 | 768 ± 123 | 2.5 ± 0.2 | <0.01 |
| 100 | 18 | 870 ± 119 | 2.9 ± 0.12 | <0.001 |
| 1000 | 18 | 647 ± 64 | 2.1 ± 0.2 | <0.001 |

As shown in the table, isophonum is 1.5 to 2.5 times more effective than diuciphonum in all doses.

The influence on humoral immunity was studied using the method of localized-in-gel hemolysis. The hybrid mice $F_1$ (CBA/C57BL$_6$) were immunized by erythrocytes of the drum in a dose of $5×10^6$ and immediately after that the substances under study were administered per os in a starch suspenstion because the low solubility of isophonum does not permit introducing this compound intraperitoneally. On the $5^{th}$ day the number of antibody-forming cells (AFC) in the spleen of the mice was calculated and the immune response stimulation index was determined as the ratio of AFC number in the test group to the AFC number in the control group. The respective data are represented in Table 2.

TABLE 2

Influence of the test substances on the accumulation of antibody-forming cells (AFC) in the spleen of mice

| Name of the preparation | Dose, μg per mouse | AFC-number in the spleen | Number of animals in the group | Immune response stimulation index | P, reliability |
|---|---|---|---|---|---|
| Control group | 0.5 ml in a starch suspension | 500 ± 50 | 12 | 1.0 | |
| Isophonum | 500 | 2800 ± 200 | 12 | 5.6 | <0.01 |
| Diuciphonum | 500 | 2250 ± 125 | 12 | 4.5 | <0.01 |

The immune response stimulation indices of isophonum and diuciphonum are reliably indistinguishable from each other. This points to the fact that both prepatations under study exert an equal action on the humoral immunity which is tested in the reaction of AFC accumulation in the spleen of mice.

The influence of the test compound on the proliferation of T-lymphocytes was studied on a model in vitro. To this end human mononucleator cells were preliminarily incubated during three hours in the presence of different concentrations of each test substance. Each test substance was studied over a wide range of its concentrations, that is from 0.01 to 5 μg/kg. As a negative control there was added a physiological 0.9 percent solution of NaCl. The results of the influence of novel compoubds on the intensity of proliferation of human lymphocytes in the cell culture in vitro are represented in Table 3.

TABLE 3

Influence of isophonum on proliferation of T-lymphocytes in the cell culture in vitro

| Dose of the preparation | Intensity of involvement of 3H-thymidine in DNA of cultivated cells (impulse per minute) | |
|---|---|---|
| μg/ml | Spontaneous | PHA-activated |
| Physiological solution | 800 | 20002 |
| Isophonum | | |
| 5 | 871 | 20120 |
| 1 | 1272 | 25455 |
| 0.1 | 1818 | 37890 |
| 0.03 | 1152 | 24736 |
| 0.01 | 901 | 19995 |
| Diuciphonum | | |
| 5 | 800 | 20150 |
| 1 | 799 | 26400 |
| 0.1 | 804 | 28946 |
| 0.03 | 850 | 24214 |
| 0.01 | 860 | 22811 |

It follows that, firstly, isophonum possesses the proper mitogenetic activitiy of its own and, secondly, it is capable of enhancing the proliferation of T-cells in response to PHA (phytohemagglutinin). The optimal concentration is 0.1 μg/ml.

The influence of the preparations in question on the phagocytic activity of macrophages was studid from clearence of the carcass in blood taken from the retroorbital sinus of mice that received the preparations per os. The results were estimated on the phagocytic index α (see Table 4).

TABLE 4

Influence of the preparations under study
on phagocytic activity of macrophages

| Name of the preparation | Dose, μg per mouse | Phagocytic index | Number of animals | P, reliability |
|---|---|---|---|---|
| Controls | 0.5 ml in a starch suspension | 4.2 ± 0.06 (100%) | 12 | |
| Isophonum | 500 | 6.55 ± 0.06 (156%) | 12 | <0.001 |
| Diuciphonum | 500 | 5.18 ± 0.04 (123%) | 12 | <0.001 |

From the results of this experiment it can be concluded that isophonum stimulates the phagocytic activity of macrophages by 56 percent.

Antituberculous activity of isophonum was tested versus the classical antituberculous preparation tubazide and the highly active immunomodulator diuciphonum. For the purpose of infecting the animals there were used laboratory ordinary and tubazide-resistant strains of tuberculosis mycobacteria $H_{37}RV$ up to 100 mg. 230 mice of the CBA line were infected intravenously with 0.25 mg of the culture of tuberculous micobacteria in 0.5 ml of physiological solution. The experiment lasted two months from the 10$^{th}$ of September to the 12$^{th}$ of November 1996. Observated were 16 groups of animals with 15 mice in each group. All the animals were kept under the same conditions of the vivarium on a standard diat.

During the course of the experiment the control groups of animals received 0.5 ml of a starch suspension through a probe five times a week. The test groups of animals received the preparations in different doses in 0.5 ml of a starch suspension. After the experiment all the animals, both the died and the killed, were weighed and so were their interior organs, the degree of damage to their interior organs was determined and, in addition, the action of the preparation was judged from the average life duration (LD). The results of the experiments are represented in Table 5.

TABLE 5

| Group, doses | USSR $H_{37}Rv$ | | |
|---|---|---|---|
| μg per mouse | Life duration | Weight of the lung | Damage index |
| Control | 24.2 ± 2.7 | 619.2 ± 50.4 | 2.48 ± 0.22 |
| Tubazide 100 | 29.4 ± 47.2 | 586.4 ± 47.2 | 2.16 ± 0.17 |
| Tubazide 200 | 32.2 ± 4.4 | 550.6 ± 46.4 | 2.11 ± 0.18 |
| Diuciphonum | 25.1 ± 2.8 | 580.4 ± 50.7 | 2.31 ± 0.24 |
| Isophonum 100 | 34.6 ± 4.8 | 507.0 ± 48.4 | 1.91 ± 0.18 |
| Isophonum 200 | 35.7 ± 5.2 | 495.4 ± 56.1 | 1.81 ± 0.21 |

| Group, doses | Tubazide-resistant $H_{37}Rv$ | | |
|---|---|---|---|
| μg per mouse | Life duration | Weight of the lung | Damage index |
| Controls | 23.8 ± 3.1 | 632.4 ± 70 | 2.42 ± 0.1 |
| Tubazide 100 | 23.7 ± 2.4 | 628.7 ± 48.4 | 2.44 ± 0.24 |
| Tubazide 200 | 30.2 ± 2.8 | 580.4 ± 46.4 | 2.01 ± 0.18 |
| Diuciphonum | 24.9 ± 2.4 | 602.7 ± 70.2 | 2.27 ± 0.19 |
| Isophonum 100 | 35.2 ± 3.4 | 493.4 ± 65.1 | 1.91 ± 0.18 |
| Isophonum 200 | 37.1 ± 6.2 | 478.2 ± 60.8 | 1.72 ± 0.24 |

As indicated by the above data, isophonum possesses a pronounced antituberculous action both on the mycobacteria that are sensitive to the most of antituberculous preparations and on the mycobacteria that are resistent to tubazide and streptomycin.

Antileprous activity of isophonum as compared with that of diuciphonum was studied on male mice of the CBA line infected with the laboratory Kyp-4 strain of leprosy mycobacteria taken in an amount of 5000 and introduced intraplantedly by Shepard's procedure. The experiment lasted six months from the 7$^{th}$ of February to the 4$^{th}$ of June 1996. Observed were 5 groups of mice with 15 mice in each group. All the animals were kept under the same conditions of the vivarium on a standard diat.

The first group (controls): during six months of the experiment the mice received 0.5 ml of a starch suspension through a probe five times a week. After six months the animals were killed through a cervical dislocation of backbone, the organs were subjected to a bacterioscopic investigation, no pathologic deviations characteristic of any of the groups were found. The bacteriscopic investigation of the infected site was carried out by grinding the mouse foot in 2 ml of 0.1 percent solution of albumin, making a smear from 0.01 ml of the suspenstion and painting it by Ziel-Nielson's procedure and counting the number of leprosy micobacteria in 60 fields of vision to determine the number of micobacteria per mouse in each group. The results of investigation are represented in Table 6.

TABLE 6

| Group | Number of mice in the group | Number of mycobacteria in the foot × 10$^6$ | Percentage of infected animals | P with respect to the controls |
|---|---|---|---|---|
| Controls | 20 | 1.14 ± 0.12 | 100% | |
| Isophonum | 20 | — | 0 | |
| Diuciphonum | 20 | 0.048 ± 0.007 | 60% | <0.1 |

As follows from the above data, isophonum in the dose studed (2.5 mg/kg) possesses bactericide activity against the leprosy mycobacteria.

Immunocorrecting and antimicrobial properties of isophonum revealed in the experiment were confimed by clinical testing of isophonum on persons suffering from leprosy (agent: mycobacteria of leprosy), on persons suffering from tuberculosis and pulmonary chronic nonspecific diseases (PCND) against the background of an immunodeficient state of the organism.

The pharmaceutical preparation of the present invention was studied clinically versus diuciphonum on people suffering from leprosy. The daily dose of the preparation was 0.6 g. Already after 3 to 4 weeks the patients who received isophonum felt an improvement of the general state of health with a decrease of inflammatory infiltrates on the skin and a change of their colour from rust-brown to pale pink. After 3 months the agent of leprosy disappeared in scrapes of nasal mucosa and the bacteriocscopic index darstically lowered. After 5 to 6 months the agent of leprosy could not be detected by bacterioscopic and histological investigation. The patients who received diuciphonum passed the same phases of clinical recovery, yet slower, because the agent of leprosy still continued to be detected by bacterioscopic and histological investigation in patients of this group some 10 to 12 months after. The results obtained are represented in Table 7.

TABLE 7

Immunologic investigation of people suffering from leprosy that were treated with isophonum (I) and diuciphonum (II)

| Group | Immunologic tests | Before treatment | After one month | After three months | P |
|---|---|---|---|---|---|
| I | T-lymphocytes | 28.6 ± 0.1 | 43.4 ± 0.7 | 60.2 ± 0.9 | <0.001 |
|   | B-lymphocytes | 8.4 ± 0.2 | 10.0 ± 0.2 | 11.4 ± 0.4 | |
|   | T-helpers | 20.2 ± 0.2 | 28.2 ± 0.3 | 48.4 ± 1.2 | |
|   | T-suppressors | 20.4 ± 0.3 | 20.0 ± 0.4 | 21.2 ± 0.4 | |
|   | Th/Ts | 1.0 ± 0.01 | 1.4 ± 0.006 | 2.3 ± 0.1 | |
| II | T-lymphocytes | 30.4 ± 0.4 | 50.5 ± 2.1 | 55.4 ± 2.4 | <0.001 |
|    | B-lymphocytes | 6.3 ± 0.3 | 8.4 ± 0.6 | 9.0 ± 0.3 | |
|    | T-helpers | 16.8 ± 0.2 | 32.4 ± 2.0 | 36.9 ± 2.3 | |
|    | T-suppressors | 17.0 ± 0.4 | 20.1 ± 0.6 | 20.0 ± 0.5 | |
|    | Th/Ts | 1.0 ± 0.003 | 1.6 ± 0.1 | 1.8 ± 0.4 | |

Explanatory note:
Th = T-helpers
Ts = T-suppressors
Th/Ts = immunoregulatory index The results of immunologic examination of the people suffering from leprosy who received treatment with isophonum and diuciphonum showed that both preparations normalize the status of the patient, i.e. both the T-lymphocytes and the T-helpers increase in number and the immunoregulatory index (ratio Th/Ts), which was lowered, is normalized. It shoud be noted that the normalization of immunologic parameters takes a smother course when isophonum is used, probably due to its affecting some other mechanisms of immunity than diuciphonum.

Thus, isophonum has shown a pronounced clinical antimycobacterial and immunotropic effect surpassing that of diuciphonum.

The use of isophonum enabled the length of stationary treatment of the leprous patients to be shortened two-fold.

The pharmaceutical preparation of the present invention will be better understand on the examples given below.

EXAMPLE 1

The male patient X, 49 years old, was admitted to a clinic with a diagnosis "border-line tuberculoid leprosy". He had been considering himself ill for two years. He supposed that he had been infected in Africa where he had worked 8 years ago and used to receive vegetables from lepers. On the skin of the back, on the skin of the lateral abdiminal surfaces, on the left hip and shin, the left temple area of the head there were yellowish-reddish papules with a rust-coloured hue and sized 1.5 times 2 cm to 4 times 6 cm with no sensitivity in ther center. Disorder of sensitivity was noted along the length of peroneal and elbow nerves. The agent of leprosy was neither detected in the scrape from the nasal mucosa nor in the lymph on the bacterioscopic investigation. The histological investigation of the skin bioptate taken from the focus of damage (plaques) showed the presence of infiltrate of BT type with separate homogeneous and granular leprosy mycobacteria. In the surface layers of derma there were multiple infiltrates and in the deeper layers of the skin there were focal and strand infiltrates. The histological index was equal to 1.1. The patient was prescribed a treatment in the form of isophonum to be taken internally 0.2 g each time twice a day. After 3.5 months all the elements (plaques) on the skin completely resolved and were replaced by hyperpigmented spots which after 4 months completely gained the colour of a normal skin. The disturbed sensitivity along the length of the elbow and peroneal nerves fully restored. The patient was not hospitalyzed and received home treatment without interrupting his work. A histological investigation carried out 3 months later failed to detect the agent of leprosy. The histological index equaled 0. When histological investigation was repeated after 7 months with the purpose of transfering the patient under dispensary observation, the agent of leprosy was not detected either, in the surface layer of the derma were noted some small infiltrates out of lymphocytes with epithelioid cells in the form of accumulations.

In deeper layers of the skin there were small infiltrates around the blood vessels. It was decided to prolong the treatment of the patient for 6 months by administering isophonum internally in combination with diuciphonum. The results of immunologic investigation of the patient X are represented in Table 8.

TABLE 8

Immunologic investigation of the patient X ("border-line tuberculoid lepra") before treatment (the day 0) and after six-month treatment (the day 180)

| Lymphocytes, % | | Leucocytes | | T-lymphocytes | | B-lymphocytes, % | |
|---|---|---|---|---|---|---|---|
| 0 | 180 | 0 | 180 | 0 | 180 | 0 | 180 |
| 1 | | 2 | | 3 | | 4 | |
| 18 | 30 | 6.1 | 6.8 | 57 | 80 | 12 | 17 |

| Lymphocytes, % | | T-helpers, % | | T-suppressors | | Immunoregulatory index | Phagocytosis |
|---|---|---|---|---|---|---|---|
| 0 | 180 | 0 | 180 | 0 | 180 | Tx | Ts |
| 1 | | 5 | | 6 | | 7 | 8 |
| 18 | 30 | 50 | 63 | 4 | 27 | 25.5   2.3 | 30   5 |

EXAMPLE 2

The female patient D., 37 years old, was admitted to a clinic with a diagnosis "bronchiectatic disease". Concomitant diseases were chronic tonsillitis, diffuse enlargement of thyroid approximately of the first or the second degree.

According to the protocol of clinical tests the patient was ordered the intake of isophonum for the periode of 30 days in a daily dose of 400 mg. On the $14^{th}$ or $15^{th}$ day of intake of the preparation the morning sputum discharge considerably diminished in quantity and changed in character from pussy to mucous, the cough ceased and the patient's general state of health and mood improved. The treatment resulted in a considerable improvement both of the patient's clinical status and general blood analysis on the $20^{th}$ day, of biochemical parameters on the $7^{th}$ or $8^{th}$ day and of immune status parameters on the $31^{st}$ day of intake of isophonum; the number of T-helpers and T-suppressors increased, the total number of T-lymphocytes, the immunoregulatory index as well the number of immunoglobulins normalized. Thus in the clinical tests isophonum exhibited a marked immunocorrecting and antimycobacterial activity.

EXAMPLE 3

The female patient I., the year of birth 1940, was admitted to a clinic with lepromatose-typed leprosy, diffuse infiltrate of the skin of the face, with multiple lepromas 1 times 3 cm in size, diffuse infiltrates of the skin of both the lower and upper limbs, with multiple lepromas of the skin of the back, the buttocks and the abdomen. She had been ill for 8 years. BIN=66.8–10.8–5.5 where BIN means bacteriological index. The hystological investigation on hospitalization showed an infiltrate of lepromatose structure (LL) with the presence of an huge number of homogeneous leprosy mycobacteria, particularly in blood vessels, which testifies the involvement of the internals (spleen, liver, bone marrow)

in the lepromatose process. HI=5,4 where HI means histological index. The patient was ordered the following treatment: 200 mg of isophonum internally twice a day, 200 mg of diuciphonum i.m. and 100 mg dimocifon internally twice a day.

After 8 months of treatment the agent of leprosy vanished in the scrape of nasal mucosa, BIN was 8.3–14.2–4.2, the immunologic parameters normalized. Atfer a year of treatment many of the infiltrates resolved and the other sharply diminished in size and became soft and elastic with their colour changed from rust-brown to cyanotic. BIN became 5.7–4.8–5.3.

The histological investigation revealed the presence of grainy mycobacteria and a small number of homogeneous ones: HI=4.8. There came lymphocytes in moderate numbers. On immunologic examination the total number of lymphocytes was found to be equal to 51%, the amount of T-lymphocytes to 85%, that of B-lymphocytes to 12% and of T-helpers to 66%, the immunoregilatory index was equal to 3.4. The patient continues to undergo treatment.

Thus in clinical tests isophonum showed high antyleprous and immunocorrecting activities both when administered alone to people suffering from leprosy and in combination with other antileprous preparaions.

It should be noted that against the background of treatment with isophonum the immunodepressive action of rifampicinum and DDS (diaminodiphenylsulfonum) which is characterisic of them when they are administered for a long time, is not exhibited; on the contrary the stimulation of cell immunity takes place.

It should be noted that the improvement in clinico-immunologicl indices brought about due to treatment with isophonum occurs on the $9^{th}$ or $10^{th}$ day of treatment, and the normatization of biochemical, hematological, immunologic indices takes place after a period of 14 to 17 days of the intake of the preparation isophonum both alone and in combination with antimycobacterial preparations. Only in one case of lepromatose type leprosy the normalization of immunologic indices could not be achieved although the normalization of biochemical and general clinical indices as well as a distinct regress in leprosous process (clinical, bacterioscopic and histomorphological) were noted, this regress coming later, though, as compared with the usual average times of regress for the rest of the patients, yet still in earlier times as compared with the patients of the control group. Thus, the results of clinical tests of isophonum obtained with patients suffering from leprosy allow it to be used both individually against the early tuberculoid forms of leprosy and in combination with diuciphonum, dimociphonum, rifampicinum and other antimycobacterial preparations for treating lepromatose type leprosy due to its immunomodulating and antimicrobial effects as well as due to easy tolerance of the patients for this remedy in a dose of 400 to 600 mg (up to 1200 mg per day) and compatibility with other preparations.

The preparation of the present invention was also studied clinically on tuberculous patients. The age of the patients was under 30 years (6 persons) and under 35 years (2 persons).

The clincal forms of pulmonary tuberculosis in the patients tested were as follows:
infiltrative tuberculosis without cavities of decay and bacterioexcretion—2 persons;
infiltrative tuberculosis with decay and bacterioexcretion—4 persons;
disseminated pulmonary tuberculosis—2 people.

The length of preparation intake was 1 to 2 months. The dose was equal to 0.6 g a day.

The control group consisting of 5 persons with infiltrative pulmonary tuberculosis received conventional treatment including isoniazide. The tolerance for the preparation claimed was good. No one of the patients exhibeted clinical, hematological signs of toxicaction. There was no change in functional indices of parenchymatous organs (liver, kidneys, pancreas). In 3 persons hospitalized with symptoms of intoxication the improvement of general physical and mental state was noted including normatization of body temperature, abatement of cough, decrease in amount of sputum excretion, improvement of appetite. The dynamics of immunologic indices of blood during treatment was as follows: the absolute number of T-lymphocytes substantially unchanged, the relative number of T-cells slightly decreased.

Thus, in the process of treatment people hospitalized with symptoms of intoxication showed the improvement of general physical and mental state, normatization of body temperature, abatement of cough, decrease in amount of sputum excretion, improvement of appetite.

The immunologic examination revealed an increase in the number of T-lymphocytes, T-helpers and a reduction in the increased number of T-suppressors (see Table 9).

On the control roentgenographic investigation of lungs there was noted a positive dynamics in the form of decrease of perifocal and pericavitary infiltration. The results are represented in Table 9.

TABLE 9

Immunologic examination of the patients suffereing from pulmonary tuberculosis that received isophonum (I) as compared with the patients of the control group that received basic therapy without isophonum (-)

| Group | Immunologic tests | Before treatment | After one month | After three months | P |
|---|---|---|---|---|---|
| I | T-lymphocytes | 42.2 ± 0.1 | 48.5 ± 1.0 | 54.8 ± 0.7 | <0.001 |
|  | B-lymphocytes | 9.0 ± 0.3 | 12.0 ± 0.8 | 11.0 ± 0.6 |  |
|  | T-helpers | 28.6 ± 0.2 | 37.4 ± 0.3 | 55.5 ± 2.0 |  |
|  | T-suppressors | 28.0 ± 1.2 | 20.0 ± 0.6 | 20.0 ± 0.4 |  |
|  | Th/Ts | 1.0 ± 0.02 | 1.85 ± 0.2 | 2.75 ± 0.04 |  |
| II | T-lymphocytes | 44.0 ± 0.5 | 50.0 ± 1.0 | 50.0 ± 0.9 | <0.05 |
|  | B-lymphocytes | 7.5 ± 0.2 | 6.2 ± 1.0 | 7.5 ± 0.2 |  |
|  | T-helpers | 30.5 ± 0.8 | 32.4 ± 0.9 | 39.5 ± 1.5 |  |
|  | T-suppressors | 20.0 ± 1.2 | 18.6 ± 0.2 | 24.3 ± 2.0 |  |
|  | Th/Ts | 1.5 ± 0.09 | 1.8 ± 0.4 | 1.8 ± 0.5 |  |

Thus, when appliled to tubercular patients, isophonum proved to be an effective immunomodulator having a marked antimycobacterial acrivity. Taking into account low toxicity of isophonum, now the dicussion is on the way as to substitute the novel isophonum for tubazide in its function as the main antituberculous remedy having a toxicity of 150 mg/kg.

The preparation of the present invention has been tested clinically on people suffering from chlamydiosis.

The investigation was carried out randomizedly by a "double blind method" on 45 patients aged 25 to 49 years.

The group I consisting of 15 patients (10 persons with pulmonary chronic nonspecific diseases (PCND), 6 of them having chronic catarrhal obstructive bronchitis and 4 having chronic catarrhal nonobstructive bronchitis; 4 persons with chlamydious infection and one person with ureaplasmic infection) received the preparation claimed as monotherapy in a daily dose of 200 mg during 30 days. The group II consisting of 15 patients (8 persons with chlamydious infection, 7 persons with PCND, 5 of them having chronic catarrhal bronchitis, 2 having bronchiectatic disease) received the preparation of the present invention as monotherapy in a daily dose of 400 mg during 30 days. The group III consisting of 15 patients (13 persons with PCND, 7 of them having chronic catarrhal nonobstructive bronchitis and 6 having chronic catarrhal obstructive bronchitis; 2 persons with chlamydious infection) received a placebo.

As a result of clinical tests of the preparation claimed it was noted as follows. 14 people of group I that received the preparation in a dose of 200 mg per day showed improvement of clinico-immunologic indices. There was a positive shift already on the $7^{th}$ or $8^{th}$ day of intake of the preparation III both in the state of the patient and on immunologic investigation, i.e. in the form of increase of the total number of T-lymphocytes, T-lymphocytes, T-helpers, normalization of the immunoregulatory index, and the amont of immunoglobulins. Only in two cases immunologic examination did not reveal any changes in spite of the positive dynamics of clinical manifestations. Probably, the reason of this could reside in an insufficient dose of the preparation. Significant improvement in the state of health of the patients right up to convalescence was observed on the $14^{th}$ to $16^{th}$ day of intaking the preparation III, and this improvement was also confirmed through hematologic examination which showed that normalization of immunologic parameters was going on. Nevertheless it was advisable to continue using the preparation for some 7 to 14 days after the onset of clinical convalescence in a maintenance dose of 100 to 200 mg per day. On the $3^{rd}$ day of intaking the preparation one patient of the group I developed signs of individual intolerance in the form of nausea and vomiting, and the preparation was canceled. In 14 persons of the group II who were given the preparation in a daily dose of 400 mg there was noted improvement of clinico-immunologic parameters which came on the $7^{th}$ to $10^{th}$ day of treatment with the preparation whereas normalization of hematologic, biochemical, immunologic indices occured on the $12^{th}$ to $14^{th}$ day of treatment. However with two of 14 patients no positive effect was achieved, as far as immunologic parameters are concerned, in spite of the significant improvement in the clinical course of disease and complete normalization of general clinical and biochemical parameters. As distinct from this, one patient suffereing from chlamydious infection showed improvement of all the hematologic indices, but even on the $20^{th}$ day of treatment there were local manifestations of disease in the form of inflammation and the presence of the agent of disease. In this connection it was reasonable to repeat the course of treatment using this preparation. In group III where the patients received a placebo two people of 15 had improvement in their general physical and mental state which however could not be confirmed through general clinical, biochmical and immunologic examination. This fact may probably be linked with lability of the nervous system of respective patients so that this could produce a psychoemotional effect with positive dynamics of disease.

Thus, the clinical tests of the preparation claimed have shown that the novel original preparation simultaneously exerts both antibacterial and immunotropic action mainly on cell immunity. The clinico-immunologic effect sets in on the $7^{th}$ or $8^{th}$ day of intaking the preparation, with significant improvement and complete normalization of clinico-immunologic parameters coming on the $15^{th}$ to $17^{th}$ day depending on severity of the course of the pathological process. The absence of the immunologic effect in 2 cases in group I and in 2 cases in group II was due to an insufficient dose of the preparation which dose can be increased while repeating the course of treatment. It should be stressed that the preparation is easily tolerated by the patients and does not have any side effects when introduced both in a dose of 200 mg and a dose of 400 mg. Only one patient developed individual intolerance for the preparation on the $3^{th}$ day in the form of nausea and vomiting. On the other hand, this was probably connected with an elevated sensitivity of the patient for the gelatinous capsules in which the preparation was used.

Thus, the high clinical effect of isophonum is achieved due to its double action, i.e. the immnunostimulating action and the antichlamydious action.

At present, there is a study nearing its completion, its purpose being to investigate the direct impact of isophonum on chlamydia, trichomonads and ureaplasmatic infections.

The method for producing a novel immunomodulator compound of the present invention exhibiting an antimycobacterial activity of isophonum is carried out by reacting equimolecular amounts of 6-methyluracyl-5-sulfochloride and isoniazide in acetonitrile at 81° C. More precisely, isophonum is produced by boiling equimolecular amounts of isonicotinic acid hydrazide and 6-methyluracyl-5-sulfochloride in anhydrous acetonitrile. The samples of isophonum maintain their properties during the period of time of 3 years.

For a better understanding of the present invention there is an example below to describe the method for producing the compound claimed.

EXAMPLE 4

N-(6-methyl-2,4-dioxo-1,2,3,4-tetrahydro-5H-pyrimidin-4-sulfon)-N'-isonicotinoylhydrazide, Hydrate A mixture of 2.74 g (0.02 mol) isonicotinic acid hydrazide and 4.49 g (0.02 mol) 6-methyluracyl-5-sulfochloride in 50 ml absolute acetonitrile is subjected to boiling for 10 hours. The mixture is filtered, the filter cake is washed with acetonitrile and then with alcohol and air-dried. This yields 7.27 g of a yelowish fine powder. The product thus obtained is crystallized out of aqueous dimethylformamide.

There have been obtained 4.94 g (76%) of white light crystalls with fp.=255 to 256° C.

Found, %: C, 38.3; H, 4.0; S, 9.2; N, 20.2.

$C_{11}H_{11}N_5O_5S \cdot H_2O$.

Calculated, %: C, 38.5; H, 3.8; S, 9.4; N, 20.4.

PMR-spectrum in dimethylsulfoxide (DMSO): (3H, uracyl) 2.36 m.d. (4H, pyridin) 7.7 m.d. 8.65 m.d. 11.53 m.d (2H, $H_2O$) 3.18 m.d.

Industrial Practicability

The immunomoduler of the present invention, exhibiting antimicrobial and antimycobacterial activities and representing N-(6-methyl-2,4-dioxo-1,2,3,4-tetrahydro-5-pyrimidinsulfon)-N'-isonicotinoylhydrazide hydrate (isophonum) is widely used in medicine as the active substance of a pharmaceutical preparation for treatment of secondry immunodeficiencies and mycobacterioses. Thus, considering a wide spectrum of immunotropic activity of isophonum as well as its antimycobacterial activity and enormously low toxicity the isophonum can be used in general medical practice such as in therapy of various diseases proceeding on the background of immunodeficiency including HIV-infection as well as in therapy of mycobacterioses (tuberculosis, leprosy and others).

What is claimed is:

1. A method of treating mycobacterial and microbacterial diseases, comprising, administering to a human or animal having a mycobacterial or microbacterial disease, an amount effective for treating a mycobacterial or microbacterial disease, of a composition comprising a compound having the structure:

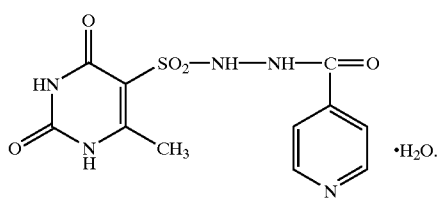
•H₂O.

2. The method of claim 1, wherein the mycobacterial or microbacterial diseases are tuberculosis, leprosy, mycobacteriosis, chronic pulmonary non-specific conditions, chlamydia, trichonosis, or ureaplasmosis.

3. The method of claim 1 wherein the effective amount comprises from approximately 0.05 g to approximately 1.2 g per day.

4. A method for producing a compound having the structure:

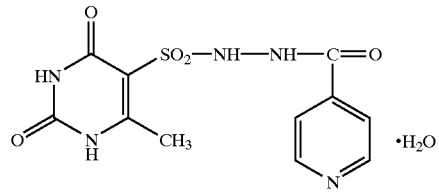
•H₂O comprising:
reacting 6-methyl uracyl-5-sulfochloride and isoniazide in a solvent at a temperature above about 81° C.

5. The method of claim 4, wherein 6-methyl uracyl-5-sulfochloride and isoniazide are reacted in equimolar amounts.

6. The method of claim 4, wherein the solvent is acetonitrile.

7. A pharmaceutical preparation, comprising, a pharmaceutically acceptable carrier and a compound having the formula:

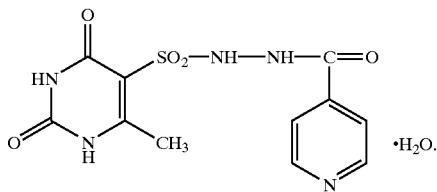
•H₂O.

8. The pharmaceutical preparation of claim 7, wherein the pharmaceutical preparation contains between 0.05 g and 0.3 g of a compound having the formula:

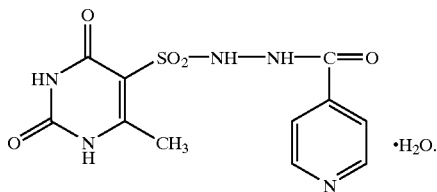
•H₂O.

* * * * *